(12) United States Patent
Robert

(10) Patent No.: US 11,814,383 B2
(45) Date of Patent: Nov. 14, 2023

(54) CRYSTALLINE IMIDAZO[4,5-B]PYRIDINE COMPOUND, PHARMACEUTICAL COMPOSITIONS, AND THEIR USE IN TREATING MEDICAL CONDITIONS

(71) Applicant: Genzyme Corporation, Cambridge, MA (US)

(72) Inventor: Benoit Robert, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/985,531

(22) Filed: Nov. 11, 2022

(65) Prior Publication Data
US 2023/0151008 A1 May 18, 2023

(30) Foreign Application Priority Data
Nov. 12, 2021 (EP) .................................. 21207942

(51) Int. Cl.
*C07D 471/04* (2006.01)
(52) U.S. Cl.
CPC ........ *C07D 471/04* (2013.01); *C07B 2200/13* (2013.01)
(58) Field of Classification Search
CPC ......................... C07B 2200/13; C07D 471/04
See application file for complete search history.

(56) References Cited

U.S. PATENT DOCUMENTS

| 9,067,914 | B1 | 6/2015 | Kane, Jr. et al. |
| 9,174,986 | B2 | 11/2015 | Kane, Jr. et al. |
| 9,611,265 | B2 | 4/2017 | Kane, Jr. et al. |
| 10,166,239 | B2 | 1/2019 | Kane, Jr. et al. |
| 10,219,998 | B2 | 3/2019 | Lieberman et al. |
| 11,110,055 | B2 | 9/2021 | Lieberman et al. |
| 11,406,644 | B2 | 8/2022 | Kane, Jr. et al. |
| 2022/0110861 | A1 | 4/2022 | Lieberman et al. |
| 2023/0080874 | A1 | 3/2023 | Kane, Jr. et al. |

FOREIGN PATENT DOCUMENTS

| WO | WO-2015089139 A1 | 6/2015 |
| WO | WO-2016100677 A2 | 6/2016 |
| WO | WO-2019084285 A1 | 5/2019 |
| WO | WO-2019191659 A1 | 10/2019 |
| WO | WO-2020038415 A1 | 2/2020 |
| WO | WO-2021170109 A1 | 9/2021 |

OTHER PUBLICATIONS

International Search Report and Written Opinion for International Application No. PCT/US2022/049695, dated Feb. 23, 2023.

*Primary Examiner* — Alicia L Otton
(74) *Attorney, Agent, or Firm* — Dechert LLP; Chad E. Davis

(57) ABSTRACT

The invention provides a crystalline imidazo[4,5-b]pyridine compound, pharmaceutical compositions, methods of inhibiting tropomyosin-related kinase and/or c-FMS, and methods of treating medical diseases and conditions, such as pain.

26 Claims, 5 Drawing Sheets

CRYSTALLINE IMIDAZO[4,5-B]PYRIDINE COMPOUND, PHARMACEUTICAL COMPOSITIONS, AND THEIR USE IN TREATING MEDICAL CONDITIONS

CROSS-REFERENCE TO RELATED APPLICATIONS

This application claims the benefit of and priority to European Patent Application serial number 21207942.0, filed Nov. 12, 2021, the contents of which are hereby incorporated by reference in their entirety.

FIELD OF THE INVENTION

The invention provides a crystalline imidazo[4,5-b]pyridine compound, pharmaceutical compositions, methods of inhibiting tropomyosin-related kinase and/or c-FMS, and methods of treating medical diseases and conditions, such as pain.

BACKGROUND

Pain can function as a protective mechanism that allows healthy human beings and animals to avoid tissue damage and/or prevent further damage to injured tissue. However, there are many instances in which pain persists beyond its usefulness. Such unnecessary suffering from pain can impair a person's physical mobility, mental performance, ability to sleep normally, to engage in occupations, and even contribute to depression. One type of pain that affects a substantial number of patients is osteoarthritis pain. Osteoarthritis pain can be debilitating. For example, patients suffering from knee osteoarthritis pain are often impaired in their ability to perform simple daily tasks such as walking or climbing stairs. The pain may be felt even while sitting in a chair or lying in bed and may interfere with ability to sleep. Long duration relief from knee osteoarthritis pain would provide a substantial benefit to patients suffering from knee osteoarthritis pain.

Compounds that inhibit tropomyosin-related kinase have been reported for use in treating pain, such as osteoarthritis pain. Tropomyosin-related kinases are high affinity receptors activated by soluble growth factors called neutrophins. Activation of a tropomyosin-related kinase leads to the activation of downstream kinases that are implicated in cell signaling, including cell proliferation, survival, angiogenesis and metastasis. International patent application publications WO 2015/089139 and WO 2016/100677 describe certain compounds that inhibit tropomyosin-related kinase. Additional compounds for inhibiting tropomyosin-related kinase and having superior properties are desirable.

The present invention addresses this need for additional compounds and provides other related advantages.

SUMMARY

The invention provides a crystalline imidazo[4,5-b]pyridine compound, pharmaceutical compositions, methods of inhibiting tropomyosin-related kinase and/or c-FMS, and methods of treating medical diseases and conditions, such as pain. For example, one aspect of the invention provides the compound crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3. Said crystalline compound may be characterized according to an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 provides the benefit that it is thermodynamically more stable than crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 may be used in pharmaceutical compositions and therapeutic methods described herein. Various aspects and embodiments are described in more detail below.

Accordingly, one aspect of the invention provides the compound 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. In certain embodiments, the X-ray powder diffraction pattern further comprises a peak at the following diffraction angle (2θ): 16.6±0.2. In certain embodiments, the X-ray powder diffraction pattern further comprises a peak at the following diffraction angle (2θ): 22.6±0.2. In certain embodiments, the X-ray powder diffraction pattern further comprises a peak at the following diffraction angle (2θ): 22.9±0.2. In certain embodiments, the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2. The compound may be part of a pharmaceutical composition comprising a pharmaceutically acceptable carrier.

Another aspect of the invention provides a method of treating a disease or condition selected from the group consisting of an inflammatory disease, autoimmune disease, pain, osteoarthritis, defect of bone metabolism, and cancer. The method comprises administering a therapeutically effective amount of a compound described herein to a subject in need thereof to treat the disease or condition. In certain embodiments, the disease or condition is pain, such as pain due to osteoarthritis. In certain embodiments, the disease or condition is osteoarthritis.

Another aspect of the invention provides a method of inhibiting the activity of a tropomyosin-related kinase. The method comprises contacting a tropomyosin-related kinase with an effective amount of a compound described herein to inhibit the activity of said tropomyosin-related kinase. In certain embodiments, the tropomyosin-related kinase is tropomyosin-related kinase A. In certain embodiments, the tropomyosin-related kinase is tropomyosin-related kinase B. In certain embodiments, the tropomyosin-related kinase is tropomyosin-related kinase C.

Another aspect of the invention provides a method of inhibiting the activity of a cellular receptor for colony stimulating factor-1. The method comprises contacting said cellular receptor for colony stimulating factor-1 with an effective amount of a compound described herein to inhibit the activity of said cellular receptor for colony stimulating factor-1.

Another aspect of the invention provides a method of preparing the compound 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. The method comprises the steps of:

a. admixing (i) a first solution containing acetone, water, and 3-(3-methoxy methoxybenzyl)oxy)benzyl)-6-(1-methyl-1H-pyrazol-4-yl)-3H-imidazo[4,5-b]pyridin-2-amine and (ii) an aliquot of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2 to provide a first mixture;

b. maintaining the first mixture at a temperature in the range of from about 45° C. to about 55° C. for a duration of at least 2 hours, to produce a crystallization mixture containing an abundance of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2; and c. isolating said compound in crystalline form from the crystallization mixture.

In certain embodiments, the ratio of acetone to water in the first solution is about 80:20 w/w. In certain embodiments, the first solution has a temperature in the range of from about 45° C. to about 55° C. Further embodiments are described herein below.

DETAILED DESCRIPTION

Figure 1:
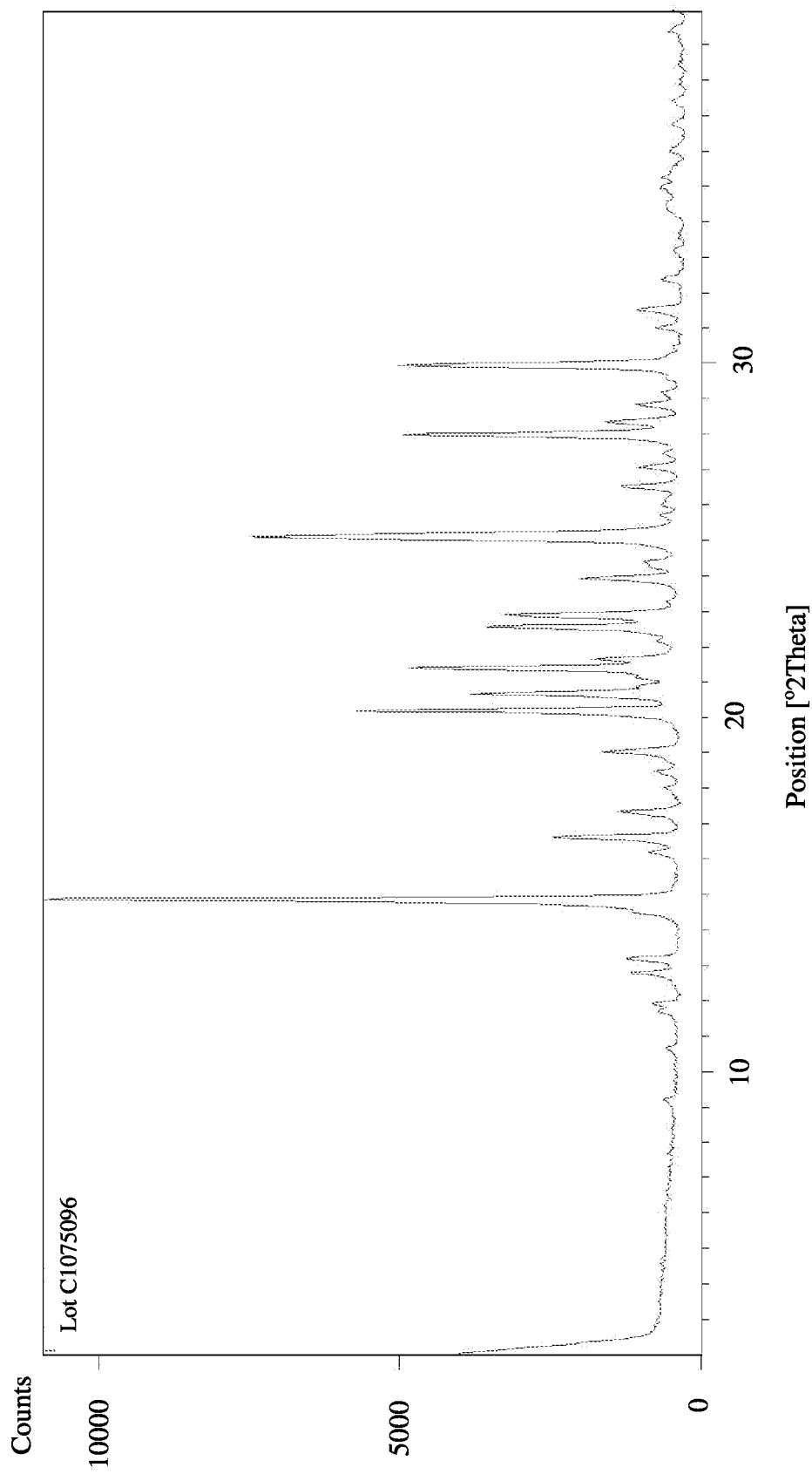
FIG. 1 depicts an X-ray powder diffractogram of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3, as further described in Example 3.

The invention provides a crystalline imidazo[4,5-b]pyridine compound, pharmaceutical compositions, methods of inhibiting tropomyosin-related kinase and/or c-FMS, and methods of treating medical diseases and conditions, such as pain. For example, one aspect of the invention provides the compound crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3. Said crystalline compound may be characterized according to an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 provides the benefit that it is thermodynamically more stable than crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 may be used in pharmaceutical compositions and therapeutic methods described herein. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates.

The terms "a" and "an" as used herein mean "one or more" and include the plural unless the context is inappropriate.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

Unless specified otherwise, the term "about" refers to within ±10% of the stated value. The invention encompasses embodiments where the value is within ±9%, ±8%, ±7%, ±6%, ±5%, ±4%, ±3%, ±2%, or ±1% of the stated value.

The chemical name "3-(3-methoxy-4-((4-methoxybenzyl)oxy)benzyl)-6-(1-methyl-1H-pyrazol-4-yl)-3H-imidazo[4,5-b]pyridin-2-amine" refers to the compound having the following formula:

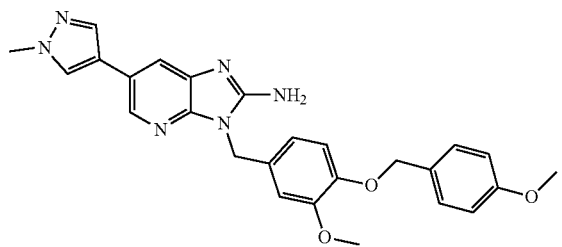

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is C1-4 alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

The invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Crystalline Imidazo[4,5-b]pyridine Compound

The invention provides a crystalline imidazo[4,5-b]pyridine compound, described herein as crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3. The crystalline imidazo[4,5-b]pyridine compound may be characterized by X-ray powder diffraction, differential scanning calorimetry, and other spectroscopic techniques. Methods for preparing and using the compound are described herein below. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 provides the benefit that it is thermodynamically more stable than crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 is described in international patent application publication WO 2016/100677.

Accordingly, one aspect of the invention provides the compound 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. In certain embodiments, the X-ray powder diffraction pattern further comprises a peak at the following diffraction angle (2θ): 16.6±0.2. In certain embodiments, the X-ray powder diffraction pattern further comprises a peak at the following diffraction angle (2θ): 22.6±0.2. In certain embodiments, the X-ray powder diffraction pattern further comprises a peak at the following diffraction angle (2θ): 22.9±0.2. In certain embodiments, the X-ray powder diffraction pattern further comprise a peak at one, two, three, four, or more of the following diffraction angles (2θ): 12.8±0.2, 13.2±0.2, 17.3±0.2, 19.0±0.2, 23.9±0.2, 26.5±0.2, 28.4±0.2, and 28.8±0.2. In certain embodiments, the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2.

In certain embodiments, the relative intensity of the peak at said diffraction angles (2θ) is at least 15%. In certain embodiments, the relative intensity of the peak at said diffraction angles (2θ) is at least 20%. In certain embodiments, the relative intensity of the peak at said diffraction angles (2θ) is at least 30%.

In certain embodiments, the compound is characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 12.78 | 6.93 | 7.3 |
| 13.19 | 6.71 | 8.1 |
| 14.87 | 5.96 | 100.0 |
| 16.62 | 5.33 | 19.3 |
| 17.34 | 5.12 | 8.9 |
| 19.03 | 4.66 | 11.8 |
| 20.19 | 4.40 | 49.1 |
| 20.67 | 4.30 | 31.0 |
| 21.40 | 4.15 | 40.7 |
| 22.56 | 3.94 | 28.6 |
| 22.90 | 3.88 | 26.1 |
| 23.93 | 3.72 | 14.4 |
| 25.09 | 3.55 | 64.4 |
| 26.53 | 3.36 | 7.4 |
| 28.00 | 3.19 | 41.6 |
| 28.35 | 3.15 | 10.5 |
| 28.83 | 3.10 | 6.2 |
| 29.95 | 2.98 | 42.4. |

In certain embodiments, the compound has an X-ray powder diffraction pattern that is substantially as shown in FIG. 1.

Figure 2:
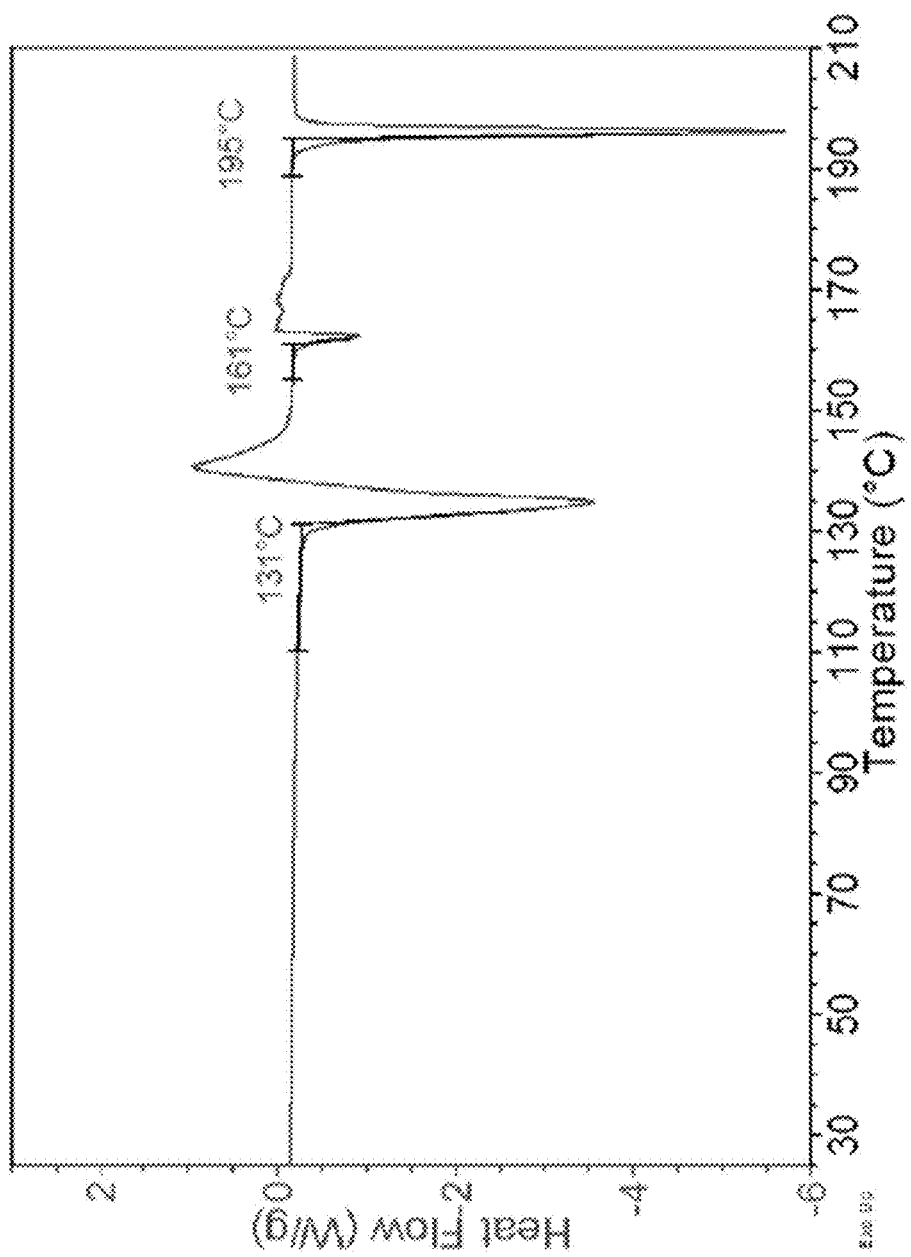
FIG. 2 depicts a differential scanning calorimetry curve of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3, as further described in Example 3.

In certain embodiments, the compound has a differential scanning calorimetry curve substantially the same as shown in FIG. 2.

The crystalline compound can be prepared, for example, by crystallization from an acetone/water solution as described in the Examples.

II. Therapeutic Applications of the Crystalline Imidazo[4,5-b]pyridine Compound and Pharmaceutical Compositions The crystalline imidazo[4,5-b]pyridine compound described herein may be used to treat inflammatory disease, autoimmune disease, pain, osteoarthritis, defect of bone metabolism, and cancer. Accordingly, one aspect of the invention provides a method of treating a disease or condition selected from the group consisting of an inflammatory disease, autoimmune disease, pain, osteoarthritis, defect of bone metabolism, and cancer. The method comprises administering a therapeutically effective amount of a compound described herein to a subject in need thereof to treat the disease or condition. The compound may be formulated as a pharmaceutical composition. Preferably, the compound is 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. In certain embodiments, the X-ray powder diffraction pattern further comprises a peak at the following diffraction angle (2θ): 16.6±0.2. In certain embodiments, the X-ray powder diffraction pattern further comprises a peak at the following diffraction angle (2θ): 22.6±0.2. In certain embodiments, the X-ray powder diffraction pattern further comprises a peak at the following diffraction angle (2θ): 22.9±0.2. In certain embodiments, the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2.

In certain embodiments, the disease or condition is an inflammatory disease. In certain embodiments, the disease or condition is autoimmune disease. In certain embodiments, the disease or condition is pain. In certain embodiments, the disease or condition is pain due to osteoarthritis. In certain embodiments, the disease or condition is joint pain due to osteoarthritis, such as knee joint pain due to osteoarthritis. In certain embodiments, the disease or condition is post-operative pain. In certain embodiments, the disease or condition is osteoarthritis. In certain embodiments, the disease or condition is cancer.

In certain embodiments, the subject is a human.

Another aspect of the invention provides a method of inhibiting the activity of a tropomyosin-related kinase. The method comprises contacting a tropomyosin-related kinase with an effective amount of a compound described herein to inhibit the activity of said tropomyosin-related kinase. In certain embodiments, the tropomyosin-related kinase is tropomyosin-related kinase A. In certain embodiments, the tropomyosin-related kinase is tropomyosin-related kinase B. In certain embodiments, the tropomyosin-related kinase is tropomyosin-related kinase C. Preferably, the compound is 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. In certain embodiments, the X-ray powder diffraction pattern further comprises a peak at the following diffraction angle (2θ): 16.6±0.2. In certain embodiments, the X-ray powder diffraction pattern further comprises a peak at the following diffraction angle (2θ): 22.6±0.2. In certain embodiments, the X-ray powder diffraction pattern further comprises a peak at the following diffraction angle (2θ): 22.9±0.2. In certain embodiments, the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2.

Another aspect of the invention provides a method of inhibiting the activity of a cellular receptor for colony stimulating factor-1. The method comprises contacting said cellular receptor for colony stimulating factor-1 with an effective amount of a compound described herein to inhibit the activity of said cellular receptor for colony stimulating factor-1. Preferably, the compound is 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. In certain embodiments, the X-ray powder diffraction pattern further comprises a peak at the following diffraction angle (2θ): 22.6±0.2. In certain embodiments, the X-ray powder diffraction pattern further comprises a peak at the following diffraction angle (2θ): 22.9±0.2. In certain embodiments, the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2.

Another aspect of the invention provides for the use of a compound described herein in the manufacture of a medicament. In certain embodiments, the medicament is for treating a disorder described herein, such as pain.

Another aspect of the invention provides for the use of a compound described herein for treating a medical disorder, such a medical disorder described herein (e.g., pain).

III. Methods of Preparing Crystalline Imidazo[4,5-b]pyridine Compound

Another aspect of the invention provides methods for preparing a crystalline imidazo[4,5-b]pyridine compound. The method generally entails crystallizing 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 from a solution containing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine.

Accordingly, one aspect of the invention provides a method of preparing of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. The method comprises the steps of:

a. admixing (i) a first solution containing acetone, water, and 3-(3-methoxy methoxybenzyl)oxy)benzyl)-6-(1-methyl-1H-pyrazol-4-yl)-3H-imidazo[4,5-b]pyridin-2-amine and (ii) an aliquot of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2 to provide a first mixture;

b. maintaining the first mixture at a temperature in the range of from about 45° C. to about 55° C. for a duration of at least 2 hours, to produce a crystallization mixture containing an abundance of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2; and c. isolating said 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2 from the crystallization mixture.

The method may be further characterized according to certain features of the method and/or additional embodiments. For example, in certain embodiments, the ratio of acetone to water in the first solution is about 80:20 w/w. In certain embodiments, the first solution has a temperature in the range of from about 45° C. to about 55° C. In certain embodiments, the first solution has a temperature of about 50° C. In certain embodiments, the first mixture has a temperature of about 50° C.

In certain embodiments, step (b) comprises maintaining the first mixture at a temperature of about 50° C. for a duration of at least 2 hours. In certain embodiments, step (b) comprises maintaining the first mixture at a temperature in the range of from about 45° C. to about 55° C. for a duration of at least 3 hours. In certain embodiments, step (b) comprises maintaining the first mixture at a temperature of about 50° C. for a duration of at least 3 hours. In certain embodiments, step (b) comprises maintaining the first mixture at a temperature in the range of from about 45° C. to about 55° C. for a duration of about 3 hours. In certain embodiments, step (b) comprises maintaining the first mixture at a temperature of about 50° C. for a duration of about 3 hours.

In certain embodiments, the method further comprises, after step (b), cooling (e.g., at a rate of about −5° C. per hour) the crystallization mixture to a temperature in the range of from about −5° C. to about 5° C., and then heating the crystallization mixture to a temperature in the range of from about 45° C. to about 55° C. In certain embodiments, the method further comprises, after step (b), cooling (e.g., at a rate of about −5° C. per hour) the crystallization mixture to a temperature in the range of from about −5° C. to about 5° C., maintaining the crystallization mixture at a temperature in the range of from about −5° C. to about 5° C. for at least one hour, and then heating the crystallization mixture to a temperature in the range of from about 45° C. to about 55° C. In certain embodiments, the method further comprises, after step (b), cooling (e.g., at a rate of about −5° C. per hour) the crystallization mixture to a temperature of about 0° C., and then heating the crystallization mixture to a temperature of about 50° C. In certain embodiments, the method further comprises, after step (b), cooling (e.g., at a rate of about −5° C. per hour) the crystallization mixture to a temperature of about 0° C., maintaining the crystallization mixture at a temperature of about 0° C. for at least one hour, and then heating the crystallization mixture to a temperature of about 50° C.

In certain embodiments, the isolating in step (c) comprises filtering the crystallization mixture to provide crystals of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2. In certain embodiments, the X-ray powder diffraction pattern further comprises a peak at the following diffraction angle (2θ): 16.6±0.2. In certain embodiments, the X-ray powder diffraction pattern further comprises a peak at the following diffraction angle (2θ): 22.6±0.2. In certain embodiments, the X-ray powder diffraction pattern further comprises a peak at the following diffraction angle (2θ): 22.9±0.2. In certain embodiments, the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2. In certain embodiments, the method further comprises washing said crystals with a solvent (e.g., a mixture of acetone and water, which more preferably is an 80:20 w/w mixture of acetone and water). In certain embodiments, the method further comprises washing said crystals with a solvent (e.g., a mixture of acetone and water, which more preferably is an 80:20 w/w mixture of acetone and water), and then drying the crystals under vacuum at a temperature less than 35° C. (e.g., for a duration of at least 4 hours).

In certain embodiments, the method further comprises admixing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine, heating the resulting solution to a temperature of from about 65° C. to about 75° C., and then cooling the resulting solution to provide the first solution. In certain embodiments, the method further comprises admixing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine, heating the resulting solution to a temperature of from about 65° C. to about 75° C., then cooling the resulting solution to a temperature of from about 50° C. to about 60° C., filtering the solution (e.g., through an about 0.1 µm to about 0.5 µm cartridge, or more preferably an about 0.2 µm cartridge), to thereby provide the first solution. In certain embodiments, said cooling to provide the first solution is performed at a rate of about −10° C. per hour.

In certain embodiments, the method further comprises admixing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine, heating the resulting solution to a temperature of about 70° C., and then cooling the resulting solution to provide the first solution.

In certain embodiments, the method further comprises admixing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine, heating the resulting solution to a temperature of about 70° C., then cooling the resulting solution to a temperature of about 55° C., filtering the solution (e.g., through an about 0.1 µm to about 0.5 µm cartridge, or more preferably an about 0.2 µm cartridge), to thereby provide the first solution. In certain embodiments, said cooling to provide the first solution is performed at a rate of about −10° C. per hour.

IV. Combination Therapy

Another aspect of the invention provides for combination therapy. The crystalline imidazo[4,5-b]pyridine compound may be used in combination with additional therapeutic agents to treat medical diseases or conditions, such as an inflammatory disease, autoimmune disease, pain, osteoarthritis, defect of bone metabolism, and cancer. In certain embodiments, the additional therapeutic agent is for treating pain. In certain embodiments, the additional therapeutic agent is for treating pain due to osteoarthritis. In certain embodiments, the additional therapeutic agent is for treating osteoarthritis.

The amount of crystalline imidazo[4,5-b]pyridine compound and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a crystalline imidazo[4,5-b]pyridine compound may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the crystalline imidazo[4,5-b]pyridine compound and the additional therapeutic agent(s) are administered in doses commonly employed when such agents are used as monotherapy for treating the disorder. In other embodiments, the crystalline imidazo[4,5-b]pyridine compound and the additional therapeutic agent(s) are administered in doses lower than the doses commonly employed when such agents are used as monotherapy for treating the disorder. In certain embodiments, the crystalline imidazo[4,5-b]pyridine compound and the additional therapeutic agent(s) are present in the same composition, which is suitable for oral administration.

In certain embodiments, the crystalline imidazo[4,5-b]pyridine compound may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the crystalline imidazo[4,5-b]pyridine compound, a pharmaceutically acceptable carrier, vehicle or diluent, and optionally at least one additional therapeutic agent listed above.

V. Exemplary Embodiments

Exemplary embodiments are provided below.

1. The compound 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2.
2. The compound of embodiment 1, wherein the X-ray powder diffraction pattern further comprises a peak at the following diffraction angle (2θ): 16.6±0.2.
3. The compound of embodiment 1 or 2, wherein the X-ray powder diffraction pattern further comprises a peak at the following diffraction angle (2θ): 22.6±0.2.
4. The compound of any one of embodiments 1-3, wherein the X-ray powder diffraction pattern further comprises a peak at the following diffraction angle (2θ): 22.9±0.2.
5. The compound of any one of embodiments 1-4, wherein the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2.
6. The compound of any one of embodiments 1-4, wherein the relative intensity of the peak at said diffraction angles (2θ) is at least 15%.
7. The compound of embodiment 1, wherein the relative intensity of the peak at said diffraction angles (2θ) is at least 20%.
8. The compound of embodiment 1, wherein the relative intensity of the peak at said diffraction angles (2θ) is at least 30%.
9. The compound of embodiment 1 characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 12.78 | 6.93 | 7.3 |
| 13.19 | 6.71 | 8.1 |
| 14.87 | 5.96 | 100.0 |
| 16.62 | 5.33 | 19.3 |
| 17.34 | 5.12 | 8.9 |
| 19.03 | 4.66 | 11.8 |
| 20.19 | 4.40 | 49.1 |
| 20.67 | 4.30 | 31.0 |
| 21.40 | 4.15 | 40.7 |
| 22.56 | 3.94 | 28.6 |
| 22.90 | 3.88 | 26.1 |
| 23.93 | 3.72 | 14.4 |
| 25.09 | 3.55 | 64.4 |
| 26.53 | 3.36 | 7.4 |
| 28.00 | 3.19 | 41.6 |
| 28.35 | 3.15 | 10.5 |
| 28.83 | 3.10 | 6.2 |
| 29.95 | 2.98 | 42.4. |

10. The compound of embodiment 1, wherein the X-ray powder diffraction pattern is substantially as shown in FIG. 1.
11. The compound of any one of embodiments 1-10, wherein the compound has a differential scanning calorimetry curve substantially the same as shown in FIG. 2.
12. A pharmaceutical composition comprising a compound of any one of embodiments 1-11 and a pharmaceutically acceptable carrier.
13. A method of treating a disease or condition selected from the group consisting of an inflammatory disease, autoimmune disease, pain, osteoarthritis, defect of bone metabolism, and cancer, comprising administering a therapeutically effective amount of a compound of any one of embodiments 1-11 to a subject in need thereof to treat the disease or condition.
14. The method of embodiment 13, wherein the disease or condition is an inflammatory disease.
15. The method of embodiment 13, wherein the disease or condition is autoimmune disease.
16. The method of embodiment 13, wherein the disease or condition is pain.
17. The method of embodiment 13, wherein the disease or condition is pain due to osteoarthritis.
18. The method of embodiment 13, wherein the disease or condition is post-operative pain.
19. The method of embodiment 13, wherein the disease or condition is osteoarthritis.
20. The method of embodiment 13, wherein the disease or condition is cancer.
21. The method of any one of embodiments 13-20, wherein the subject is a human.
22. A method of inhibiting the activity of a tropomyosin-related kinase, comprising contacting a tropomyosin-related kinase with an effective amount of a compound of any one of embodiments 1-11 to inhibit the activity of said tropomyosin-related kinase.

23. The method of embodiment 22, wherein the tropomyosin-related kinase is tropomyosin-related kinase A.
24. The method of embodiment 22, wherein the tropomyosin-related kinase is tropomyosin-related kinase B.
25. The method of embodiment 22, wherein the tropomyosin-related kinase is tropomyosin-related kinase C.
26. A method of inhibiting the activity of a cellular receptor for colony stimulating factor-1, comprising contacting said cellular receptor for colony stimulating factor-1 with an effective amount of a compound of any one of embodiments 1-11 to inhibit the activity of said cellular receptor for colony stimulating factor-1.
27. A method of preparing a compound of embodiment 1, comprising the steps of:
   a. admixing (i) a first solution containing acetone, water, and 3-(3-methoxy methoxybenzyl)oxy)benzyl)-6-(1-methyl-1H-pyrazol-4-yl)-3H-imidazo[4,5-b]pyridin-2-amine and (ii) an aliquot of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2 to provide a first mixture;
   b. maintaining the first mixture at a temperature in the range of from about 45° C. to about 55° C. for a duration of at least 2 hours, to produce a crystallization mixture containing an abundance of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2; and
   c. isolating said compound of embodiment 1 from the crystallization mixture.
28. The method of embodiment 27, wherein the ratio of acetone to water in the first solution is about 80:20 w/w.
29. The method of embodiment 27 or 28, wherein the first solution has a temperature in the range of from about 45° C. to about 55° C.
30. The method of embodiment 27 or 28, wherein the first solution has a temperature of about 50° C.
31. The method of any one of embodiments 27-30, wherein the first mixture has a temperature of about 50° C.
32. The method of any one of embodiments 27-31, further comprising admixing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine, heating the resulting solution to a temperature of from about 65° C. to about 75° C., and then cooling the resulting solution to provide the first solution.
33. The method of embodiment 32, wherein said cooling to provide the first solution is performed at a rate of about −10° C. per hour.

VI. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In certain embodiments, the invention provides a pharmaceutical composition comprising a crystalline imidazo[4,5-b]pyridine compound described herein and a pharmaceutically acceptable carrier.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a crystalline imidazo[4,5-b]pyridine compound described herein in a therapeutically effective amount for the treatment of a medical disease or condition described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Preparation of Crystalline 3-(3-methoxy-4-((4-methoxybenzyl)oxy) benzyl)-6-(1-methyl-1H-pyrazol-4-yl)-3H-imidazo[4,5-b]pyridin-2-amine Monohydrate Form 3

The title compound was prepared according to the following procedure. A suspension of sesquihydrate 3-(3-methoxy-4-((4-methoxybenzyl)oxy)benzyl)-6-(1-methyl-1H-pyrazol-4-yl)-3H-imidazo[4,5-b]pyridin-2-amine in a mixture of acetone and water (where the mixture was 80/20 w/w acetone to water) was heated at a temperature of 50° C., without stirring. Thereafter, from the resulting mixture, crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3 was isolated.

The sesquihydrate 3-(3-methoxy-4-((4-methoxybenzyl) oxy)benzyl)-6-(1-methyl-1H-pyrazol-4-yl)-3H-imidazo[4,5-b]pyridin-2-amine starting material used in this example is described in international patent application publication WO 2016/100677.

Example 2—Preparation of Crystalline 3-(3-methoxy-4-((4-methoxybenzyl)oxy) benzyl)-6-(1-methyl-1H-pyrazol-4-yl)-3H-imidazo[4,5-b]pyridin-2-amine Monohydrate Form 3

The title compound was prepared according to the following procedure. 3-(3-Methoxy-4-((4-methoxybenzyl) oxy)benzyl)-6-(1-methyl-1H-pyrazol-4-yl)-3H-imidazo[4,5-b]pyridin-2-amine was dissolved in 80/20 w/w mixture of acetone and water heated to a temperature of 70° C. The resulting solution was cooled to a temperature of 55° C. and then filtered through a 0.2 µm cartridge. The filtered solution was cooled to a temperature of 50° C. (where cooling was performed at a rate of −10° C. per hour), and then solution was seeded with 2% by weight crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3. The resulting mixture was maintained at 50° C. for at least 3 hours, and then two cooling/heating cycles were performed to increase the size of the crystals. Each heating/cooling cycle involved first cooling the mixture to 0° C. (where cooling was performed at a rate of −5° C. per hour), holding the temperature of the mixture at 0° C. for 1 hour, then heating the mixture to a temperature of 50° C. After completing the two cooling/heating cycles, crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 was isolated from the mixture using a filter dryer, washed twice with an 80/20 w/w mixture of acetone/water, and then dried under vacuum for at least 4 hours while maintaining the temperature below 35° C. to provide the final material that is crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3.

Example 3—Physical Characterization of Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 3

Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 was characterized by X-ray powder diffraction, single crystal X-ray diffraction, differential scanning calorimetry, dynamic vapor sorption, thermogravimetric analysis/mass spectrometry (TGA-MS), and particle morphology. Results are provided below.

X-Ray Powder Diffraction

An X-ray powder diffractogram taken on crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 is provided in FIG. 1. Tabulated characteristics of the X-ray powder diffractogram in FIG. 1 are provided in the following table, which lists diffraction angle 2θ, inter-planar distances d, and relative intensity (expressed as a percentage with respect to the most intense peak):

| Angle [2θ] | d-spacing [Å] | Relative Intensity [%] |
| --- | --- | --- |
| 12.78 | 6.93 | 7.3 |
| 13.19 | 6.71 | 8.1 |
| 14.87 | 5.96 | 100.0 |
| 16.62 | 5.33 | 19.3 |
| 17.34 | 5.12 | 8.9 |
| 19.03 | 4.66 | 11.8 |
| 20.19 | 4.40 | 49.1 |
| 20.67 | 4.30 | 31.0 |
| 21.40 | 4.15 | 40.7 |
| 22.56 | 3.94 | 28.6 |
| 22.90 | 3.88 | 26.1 |
| 23.93 | 3.72 | 14.4 |
| 25.09 | 3.55 | 64.4 |
| 26.53 | 3.36 | 7.4 |

-continued

| Angle [2θ] | d-spacing [Å] | Relative Intensity [%] |
|---|---|---|
| 28.00 | 3.19 | 41.6 |
| 28.35 | 3.15 | 10.5 |
| 28.83 | 3.10 | 6.2 |
| 29.95 | 2.98 | 42.4 |

Single Crystal X-Ray Diffraction

A crystal of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 was characterized by single crystal X-ray diffraction. The crystal structure was determined by XRSCD at 27° C. A monoclinic lattice was determined, with space group C2/c. Lattice parameters of the crystal are the following:

| Monoclinic Pn | | | |
|---|---|---|---|
| a = | 19.35 Å | α = γ = | 90° |
| b = | 10.76 Å | β = | 102.40° |
| c = | 31.92 Å | | |
| V = | 6485 Å³ | d = | 1.12 |

Differential Scanning Calorimetry

A differential scanning calorimetry curve of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 is provided in FIG. 2. The mass loss at temperature 130° C. corresponds to departure of 1 molecule of water.

Dynamic Vapor Sorption

Figure 3:
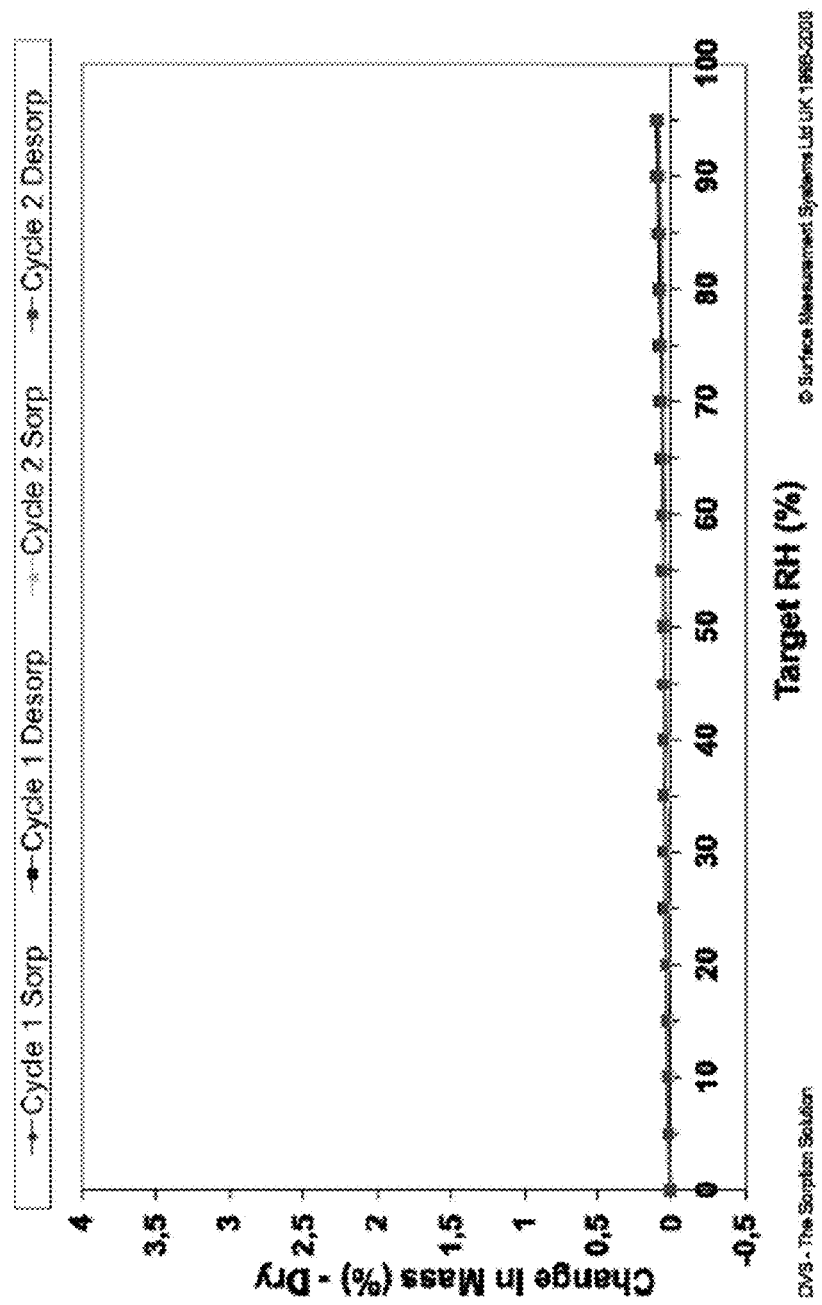
FIG. 3 depicts a DVS isotherm plot of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3, as further described in Example 3.

A dynamic vapor sorption isotherm plot of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 is provided in FIG. 3. The dynamic vapor sorption isotherm plot results are from the procedure where after a drying stage at 0% relative humidity, compound sample was exposed to 2 cycles of increasing and decreasing relative humidity at 25° C., with steps of 5% relative humidity, where mass of the sample was recorded throughout the experiment.

The results demonstrate that crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3 is not hygroscopic.

Thermogravimetric Analysis/Mass Spectrometry (TGA-MS)

Figure 4:
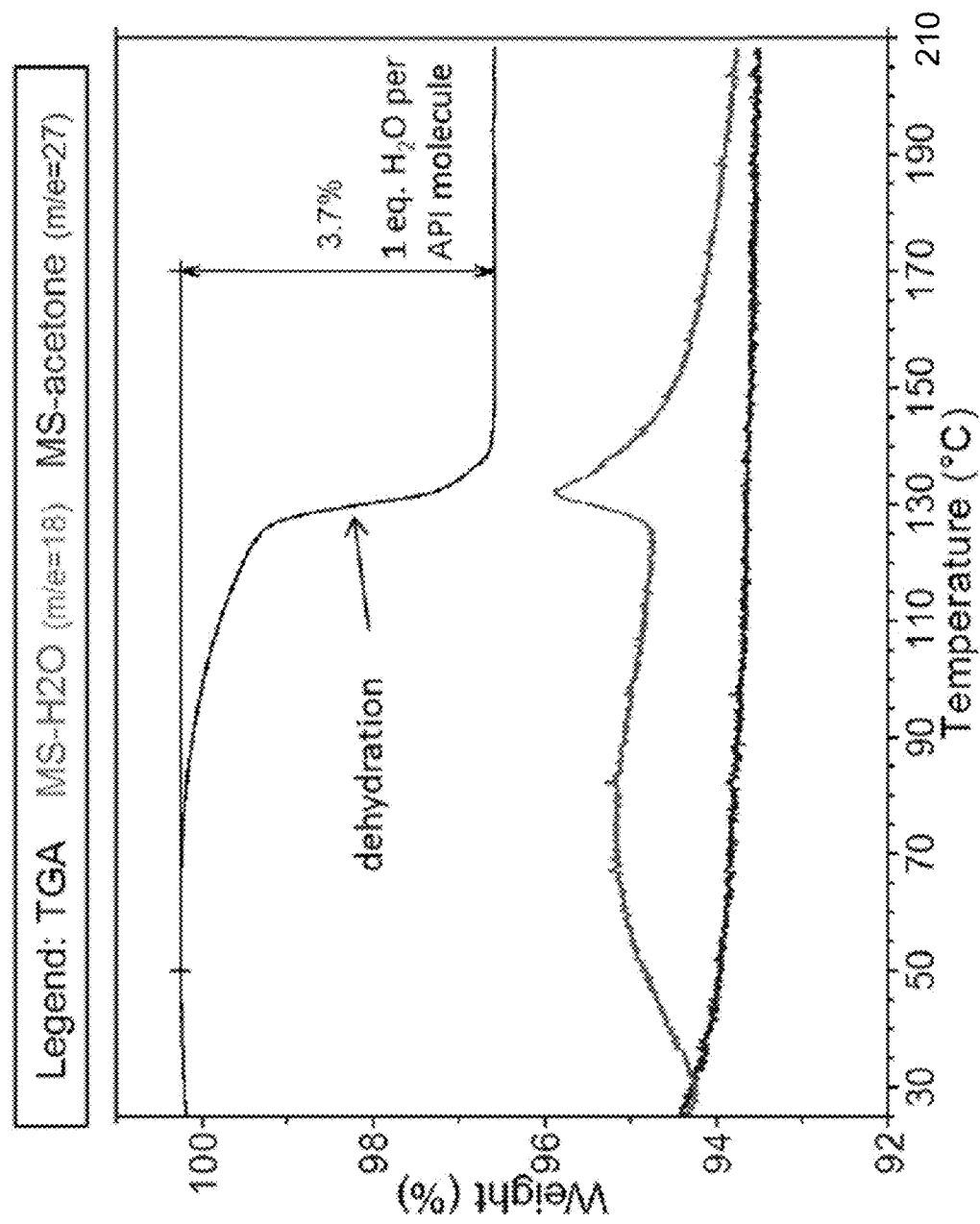
FIG. 4 depicts a thermogravimetric analysis/mass spectrometry (TGA-MS) profile of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3, as further described in Example 3.

The TGA-MS profile of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 is provided in FIG. 4. The mass profile exhibited a step at 130° C. The mass loss of 3.7% corresponds to departure of one molecule of water per 3-(3-methoxy-4-((4-methoxybenzyl)oxy) benzyl)-6-(1-methyl-1H-pyrazol-4-yl)-3H-imidazo[4,5-b]pyridin-2-amine, and reflects dehydration of the 3-(3-methoxy-4-((4-methoxybenzyl)oxy)benzyl)-6-(1-methyl-1H-pyrazol yl)-3H-imidazo[4,5-b]pyridin-2-amine monohydrate.

Particle Morphology

Particles of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 were determined to include particles having a rod shape. Rod-shaped particles provide the advantage of better flowability in dry particulate form. The rod-shaped particles also provide the advantage of better filtration when filtering a liquid suspension containing said particles.

Example 4—Comparison of Stability of Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 3 to Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 1

Stability of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 was compared to crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1. The physical property analyzed was temperature of dehydration. Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 is that described in international patent application publication WO 2016/100677.

Crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 was observed to undergo dehydration at room temperature under a stream of nitrogen gas.

By contrast, crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 did not undergo dehydration until heated to a temperature of 130° C.

Example 5—Analysis of Dialysis Dissolution of Crystalline 3-(3-methoxy-4-((4-methoxybenzyl)oxy) benzyl)-6-(1-methyl-1H-pyrazol-4-yl)-3H-imidazo[4,5-b]pyridin amine Monohydrate Form 3 and Crystalline 3-(3-methoxy-4-((4-methoxybenzyl)oxy) benzyl)-6-(1-methyl-1H-pyrazol-4-yl)-3H-imidazo[4,5-b]pyridin-2-amine Monohydrate Form 1 in Simulated Intra-Articular Fluid Dialysis dissolution of the following Test Compositions in simulated intra-articular fluid was analyzed:
Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 3, and
Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 1.

Procedurally, Test Composition was placed into a dialysis bag along with Medium A. The dialysis bag was then closed and placed into a closed bottle containing Medium B. Medium A and B were preheated to 37° C. before use in the experiment. The closed bottles were placed into a rotating mixer system operating at 20 RPM so as to avoid suspension sedimentation inside the dialysis bag. An aliquot of Medium B from the bottle was removed at the following time points and analyzed by high-performance liquid chromatography with UV detection to determine the amount of 3-(3-methoxy-4-((4-methoxybenzyl)oxy)benzyl)-6-(1-methyl-1H-pyrazol-4-yl)-3H-imidazo[4,5-b]pyridin-2-amine in Medium B due to dialysis dissolution of the Test Composition from Medium A through the dialysis bag to Medium B: 3 hr, 6 hr, 24 hr, 29 hr, 48 hr, 72 hr, 144 hr, 168 hr, 192 hr, 216 hr, and 240 hr. One Test Composition was analyzed at the 360 hour timepoint. Medium A was bovine serum albumin (BSA) at 40 g/L (+0.2 g/L sodium azide), sodium hyaluronate at 3 g/L in reconstituted phosphate buffer saline pH 7.4. Medium B was bovine serum albumin (BSA) at 40 g/L (+0.2 g/L sodium azide) in reconstituted phosphate buffer saline pH 7.4.

Figure 5:
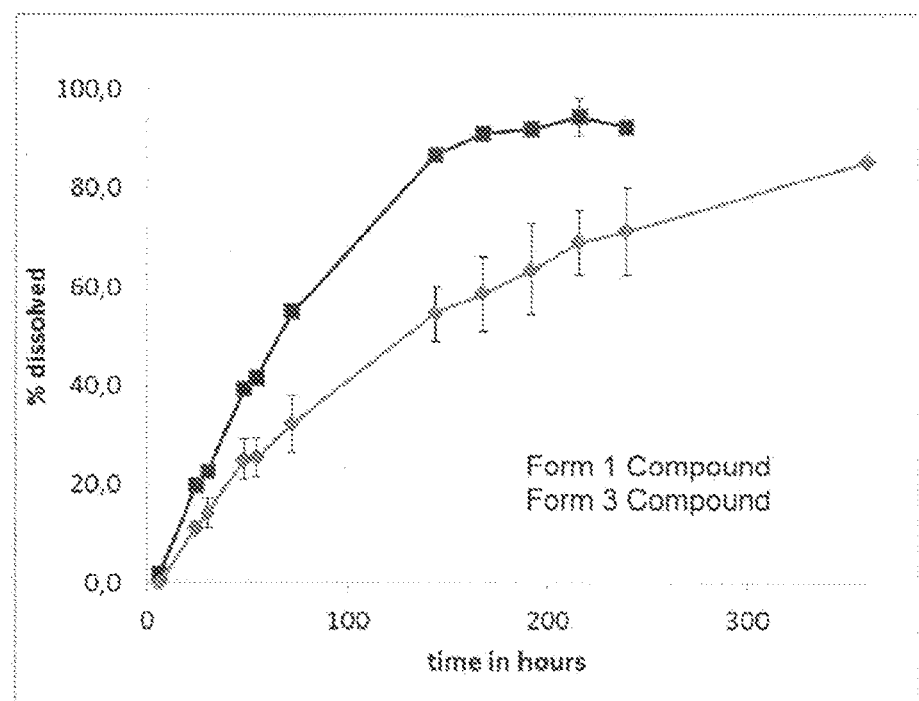
FIG. 5 is a graph showing results of a dialysis dissolution experiment evaluating dialysis dissolution of the following Test Compositions in a solution that simulates intra-articular fluid: Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 3 ("Form 3 Compound"), and Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 1 ("Form 1 Compound"), as further described in Example 5.

The determined percent dissolution of each Test Composition over time is displayed in FIG. 5. The data in FIG. 5 show that the dialysis dissolution rate was significantly lower for crystalline 3-(3-methoxy-4-((4-methoxybenzyl) oxy)benzyl)-6-(1-methyl-1H-pyrazol-4-yl)-3H-imidazo[4,5-b]pyridin-2-amine monohydrate Form 3 compared to crystalline 3-(3-methoxy-4-((4-methoxybenzyl)oxy)benzyl)-6-(1-methyl-1H-pyrazol-4-yl)-3H-imidazo[4,5-b]pyridin amine Monohydrate Form 1. For example, the data in FIG. 5 show that the one-half dissolution time was 66 hours for crystalline 3-(3-methoxy-4-((4-methoxybenzyl)oxy)benzyl) (1-methyl-1H-pyrazol-4-yl)-3H-imidazo[4,5-b]pyridin-2-amine monohydrate Form 1, whereas the one-half dissolution time was 112 hours for crystalline 3-(3-methoxy-4-((4-methoxybenzyl) oxy)benzyl)-6-(1-methyl-1H-pyrazol-4-yl)-3H-imidazo[4,5-b]pyridin-2-amine monohydrate Form 3.

Additionally, the data in FIG. 5 show that at the 7 day time point, the average release rate was 0.54%/hr for crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1, whereas the average release rate was 0.35%/hr for crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3.

Example 6—Pharmacokinetic Analysis of Crystalline 3-(3-methoxy-4-((4-methoxybenzyl)oxy)benzyl)-6-(1-methyl-1H-pyrazol-4-yl)-3H-imidazo[4,5-b]pyridin-2-amine Monohydrate Form 3 and Crystalline 3-(3-methoxy-4-((4-methoxybenzyl)oxy) benzyl)-6-(1-methyl-1H-pyrazol-4-yl)-3H-imidazo [4,5-b]pyridin-2-amine Monohydrate Form 1 after Intra-Articular Administration to Rats Male rats were administered one of the following Test Articles via intra-articular administration to the left knee joint and thereafter pharmacokinetic properties were monitored: crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 3 ("Form 3 Compound") or crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 ("Form 1 Compound"). Experimental procedures and results are provided below.

Part I—Experimental Procedure

Male Sprague Dawley rats were allocated into four groups, where each group contained 12 rats having a weight in the range of 250 g to 300 g and an age of 7 to 9 weeks. Test Article was administered in the form of a suspension via intra-articular injection to the left knee joint of the rats according to the experimental design set forth in Table 1 below.

TABLE 1

Experimental Design.

| Group No. | Test Article in the Form of a Suspension | Dose Amount Administered to Each Rat |
|---|---|---|
| 1 | Suspension of crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3 | 0.1 mg of crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3 |
| 2 | Suspension of crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3 | 1 mg of crystalline 3-(3-methoxy-4-((4-methoxybenzyl)oxy) benzyl)-6-(1-methyl-1H-pyrazol-4-yl)-3H-imidazo[4,5-b]pyridin-2-amine monohydrate Form 3 |
| 3 | Suspension of crystalline 3-(3-methoxy-4-((4-methoxybenzyl) oxy)benzyl)-6-(1-methyl-1H-pyrazol-4-yl)-3H-imidazo[4,5-b]pyridin-2-amine monohydrate Form 1 | 0.1 mg of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 |
| 4 | Suspension of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 | 1 mg of crystalline 3-(3-methoxy-4-((4-methoxybenzyl)oxy)benzyl)-6-(1-methyl-1H-pyrazol-4-yl)-3H-imidazo[4,5-b]pyridin-2-amine monohydrate Form 1 |

Each Test Article contained the specified methoxy-4-((4-methoxybenzyl) oxy)benzyl)-6-(1-methyl-1H-pyrazol-4-yl)-3H-imidazo[4,5-b]pyridin-2-amine monohydrate compound suspended in vehicle. Vehicle was 2% povidone K17, 4.5% sorbitol, in aqueous phosphate buffer at pH 7.4. Each Test Article in the form of a suspension contained 20 mg/mL methoxy-4-((4-methoxy-benzyl)oxy)benzyl)-6-(1-methyl-1H-pyrazol-4-yl)-3H-imidazo[4,5-b]pyridin-2-amine monohydrate in the specified crystalline form.

Blood samples were collected from the jugular vein of the rats via syringe and needle and transferred into tubes containing $K_3$EDTA. Blood samples were collected from the first six animals/group at 2 minutes, 10 minutes, 1 hr, 4 hr, 12 hr, 72 hr, 336 hr, and 672 hr after administration of Test Article. Blood samples were collected from the second six animals/group at 5 minutes, 0.5 hr, 2 hr, 8 hr, 24 hr, 168 hr, 1008 hr, and 1344 hr after administration of Test Article. Following centrifugation of the blood samples, plasma was cooled using dry ice until it was subjected to analytical analysis using liquid chromatograph-mass spectrometry to determine the amount of the compound methoxy-4-((4-methoxybenzyl) oxy)benzyl)-6-(1-methyl-1H-pyrazol-4-yl)-3H-imidazo[4,5-b]pyridin-2-amine.

The left knee joint (without injuring the articular capsule) of the rats together with 5-10 mm of both tibia and femur was collected from the first 6 animals/group after sacrifice at the last blood collection time point at approximately 672 hours postdose. The harvested knee joint was weighed. The left knee joint (without injuring the articular capsule) of the rats together with 5-10 mm of both tibia and femur was collected from the second 6 animals/group after sacrifice at the last blood collection time point at approximately 1344 hours postdose. The harvested knee joint was weighed. Tissue samples were maintained on dry ice prior to storage at −60 to −80° C. The knee joint samples were pulverized, then extracted with acetonitrile/water to provide a solution that was analyzed by using liquid chromatograph-mass spectrometry to determine the amount of the compound methoxy-4-((4-methoxybenzyl) oxy)benzyl)-6-(1-methyl-1H-pyrazol-4-yl)-3H-imidazo[4,5-b]pyridin-2-amine.

Part II—Results

Results for observed pharmacokinetic parameters in plasma are shown in Tables 2 and 3 below. Mean knee concentration of the compound methoxy-4-((4-methoxybenzyl) oxy)benzyl)-6-(1-methyl-1H-pyrazol-4-yl)-3H-imidazo[4,5-b]pyridin-2-amine is provided in Table 4 below. The ratio of observed knee/plasma concentration of the compound methoxy-4-((4-methoxybenzyl) oxy)benzyl)-6-(1-methyl-1H-pyrazol-4-yl)-3H-imidazo[4,5-b]pyridin-2-amine is provided in Table 5 below.

TABLE 2

Pharmacokinetic Parameters in Plasma.

| Dose Amount of Compound (mg/knee) | Group | Compound Form | Parameter | $C_{max}$ (ng/mL) | $t_{max}$ (h) | $AUC_{0-672}$ (ng·h/mL) | $AUC_{0-1344}$* (ng·h/mL) | $AUC_{0-inf}$ (ng·h/mL) |
|---|---|---|---|---|---|---|---|---|
| 0.1 | 1 | Form 3 Compound | Mean CV % | 11.4 29 | 4.0 (1.0-8.0) | 686 14 | 813 15 | 757 16 |
|  | 3 | Form 1 Compound | Mean CV % | 34.3 21 | 4.0 (2.0-8.0) | 1350 22 | 1330 23 | 1290 28 |
| 1 | 2 | Form 3 Compound | Mean CV % | 52.1 29 | 4.0 (2.0-12.0) | 5240 13 | 7100 12 | 8040 19 |
|  | 4 | Form 1 Compound | Mean CV % | 71.6 23 | 4.0 (2.0-8.0) | 10600 60 | 11100 10 | 11800 54 |

*Summary from second six animals.
CV % refers to coefficient of variation.

TABLE 3

Pharmacokinetic Parameters in Plasma.

| Dose Amount of Compound (mg/knee) | Group | Treatment | Ratio Result from Compound Form 3/Compound Form 1 | | | |
|---|---|---|---|---|---|---|
|  |  |  | $C_{max}$ | $AUC_{0-672}$ | $AUC_{0-1344}$* | $AUC_{0-inf}$ |
| 0.1 | 1 | Form 3 Compound | 0.332 | 0.508 | 0.611 | 0.587 |
| 1 | 2 | Form 3 Compound | 0.728 | 0.494 | 0.640 | 0.681 |

TABLE 4

Mean Knee Concentration of the Compound Methoxy-4-((4-methoxybenzyl) oxy)benzyl)-6-(1-methyl-1H-pyrazol-4-yl)-3H-imidazo[4,5-b]pyridin-2-amine.

| Dose Amount of Compound (mg/knee) | Group | Compound Form | Parameter | Mean Knee Concentration of Compound (ng/g) Over Nominal Time (hours) | | Ratio of Form 3 Compound/Form 1 Compound | |
|---|---|---|---|---|---|---|---|
|  |  |  |  | 672 hr | 1344 hr | 672 hr | 1344 hr |
| 0.1 | 1 | Form 3 Compound | Mean CV % | 4790 80 | 383 245 | 5.62 NA | NC NA |
|  | 3 | Form 1 Compound | Mean CV % | 852 157 | <LLOQ NC | NA NA | NA NA |

TABLE 4-continued

Mean Knee Concentration of the Compound Methoxy-4-((4-methoxybenzyl)oxy)benzyl)-6-(1-methyl-1H-pyrazol-4-yl)-3H-imidazo[4,5-b]pyridin-2-amine.

| Dose Amount of Compound (mg/knee) | Group | Compound Form | Parameter | Mean Knee Concentration of Compound (ng/g) Over Nominal Time (hours) | | Ratio of Form 3 Compound/ Form 1 Compound | |
|---|---|---|---|---|---|---|---|
| | | | | 672 hr | 1344 hr | 672 hr | 1344 hr |
| 1 | 2 | Form 3 Compound | Mean | 202000 | 62200 | 5.40 | 13.6 |
| | | | CV % | 20 | 43 | NA | NA |
| | 4 | Form 1 Compound | Mean | 37400 | 4560 | NA | NA |
| | | | CV % | 76 | 73 | NA | NA |

NC refers to not calculated.
NA refers to not applicable.
LLOQ refers to the Lower limit of quantification (100 ng/mL).

TABLE 5

Ratio of Observed Knee/Plasma Concentration of the Compound Methoxy-4-((4-methoxybenzyl)oxy)benzyl)-6-(1-methyl-1H-pyrazol-4-yl)-3H-imidazo[4,5-b]pyridin-2-amine.

| Dose Amount of Compound (mg/knee) | Group | Compound Form | Parameter | Mean Knee/Plasma Concentration Ratio Over Nominal Time (hr) | | Ratio of Form 3 Compound/ Form 1 Compound | |
|---|---|---|---|---|---|---|---|
| | | | | 672 hr | 1344 hr | 672 hr | 1344 hr |
| 0.1 | 1 | Form 3 Compound | Mean | 43100 | 77400 | 0.733 | NC |
| | | | CV % | 31 | NC | NA | NA |
| | 3 | Form 1 Compound | Mean | 58800 | NC | NA | NA |
| | | | CV % | NC | NC | NA | NA |
| 1 | 2 | Form 3 Compound | Mean | 58300 | 37200 | 2.64 | 1.96 |
| | | | CV % | 18 | 35 | NA | NA |
| | 4 | Form 1 Compound | Mean | 22100 | 19000 | NA | NA |
| | | | CV % | 44 | 55 | NA | NA |

NC refers to not calculated.
NA refers to not applicable.

Results in the above tables show that absorption was slower and more prolonged for the Form 3 Compound compared to the Form 1 Compound. The plasma Cmax was from 1.4 to 3.0-fold less for the Form 3 Compound compared to the Form 1 Compound. The plasma AUC was from 1.7 to 2.0-fold less for the Form 3 Compound compared to the Form 1 Compound. There was a 2.4 to 2.8-fold longer terminal half-life for the Form 3 Compound compared to the Form 1 Compound. Additionally, the mean residence time was from 2.7 to 3.7-fold longer for Form 3 Compound compared to the Form 1 Compound.

It was observed that when administering a 0.1 mg dose of compound, the knee concentration of compound methoxy-4-((4-methoxybenzyl) oxy)benzyl)-6-(1-methyl-1H-pyrazol-4-yl)-3H-imidazo[4,5-b]pyridin-2-amine at 672 hours was consistently higher than the concentration of methoxy-4-((4-methoxybenzyl)oxy)benzyl)-6-(1-methyl-1H-pyrazol-4-yl)-3H-imidazo[4,5-b]pyridin-2-amine in plasma in the majority of animals that received Form 3 Compound, while the knee concentration of compound methoxy-4-((4-methoxybenzyl) oxy)benzyl)-6-(1-methyl-1H-pyrazol-4-yl)-3H-imidazo[4,5-b]pyridin-2-amine was below the limit of quantification in the majority of animals that received Form 1 Compound.

It was also observed that when administering a 1 mg dose of compound, the knee concentration of compound methoxy-4-((4-methoxybenzyl)oxy)benzyl)-6-(1-methyl-1H-pyrazol-4-yl)-3H-imidazo[4,5-b]pyridin-2-amine was from 5.40 to 13.6-fold higher in animals that received Form 3 Compound compared to animals that received Form 1 Compound.

When administering a 1 mg dose of compound, the knee/plasma concentration ratio of compound methoxy-4-((4-methoxybenzyl)oxy)benzyl)-6-(1-methyl-1H-pyrazol-4-yl)-3H-imidazo[4,5-b]pyridin-2-amine was 1.96 to 2.64-fold higher in animals that received Form 3 Compound compared to animals that received Form 1 Compound.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. The compound 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2.

2. The compound of claim 1, wherein the X-ray powder diffraction pattern further comprises a peak at the following diffraction angle (2θ): 16.6±0.2.

3. The compound of claim 2, wherein the X-ray powder diffraction pattern further comprises a peak at the following diffraction angle (2θ): 22.6±0.2.

4. The compound of claim 3, wherein the X-ray powder diffraction pattern further comprises a peak at the following diffraction angle (2θ): 22.9±0.2.

5. The compound of claim 4, wherein the X-ray powder diffraction pattern further comprises peaks at the following diffraction angles (2θ): 12.8±0.2, 13.2±0.2, 17.3±0.2, 19.0±0.2, 23.9±0.2, 26.5±0.2, 28.4±0.2, and 28.8±0.2.

6. The compound of claim 4, wherein the relative intensity of the peak at said diffraction angles (2θ) is at least 15%.

7. The compound of claim 1, wherein the relative intensity of the peak at said diffraction angles (2θ) is at least 20%.

8. The compound of claim 1, wherein the relative intensity of the peak at said diffraction angles (2θ) is at least 30%.

9. The compound of claim 1 characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 12.78 | 6.93 | 7.3 |
| 13.19 | 6.71 | 8.1 |
| 14.87 | 5.96 | 100.0 |
| 16.62 | 5.33 | 19.3 |
| 17.34 | 5.12 | 8.9 |
| 19.03 | 4.66 | 11.8 |
| 20.19 | 4.40 | 49.1 |
| 20.67 | 4.30 | 31.0 |
| 21.40 | 4.15 | 40.7 |
| 22.56 | 3.94 | 28.6 |
| 22.90 | 3.88 | 26.1 |
| 23.93 | 3.72 | 14.4 |
| 25.09 | 3.55 | 64.4 |
| 26.53 | 3.36 | 7.4 |
| 28.00 | 3.19 | 41.6 |
| 28.35 | 3.15 | 10.5 |
| 28.83 | 3.10 | 6.2 |
| 29.95 | 2.98 | 42.4. |

10. The compound of claim 1, wherein the X-ray powder diffraction pattern is substantially as shown in FIG. 1.

11. The compound of claim 9, wherein the compound has a differential scanning calorimetry curve substantially the same as shown in FIG. 2.

12. A pharmaceutical composition comprising a compound of claim 1 and a pharmaceutically acceptable carrier.

13. A method of treating a disease or condition selected from the group consisting of an inflammatory disease, autoimmune disease, pain, osteoarthritis, defect of bone metabolism, and cancer, comprising administering a therapeutically effective amount of a compound of claim 1 to a subject in need thereof to treat the disease or condition.

14. The method of claim 13, wherein the disease or condition is an inflammatory disease.

15. The method of claim 13, wherein the disease or condition is autoimmune disease.

16. The method of claim 13, wherein the disease or condition is pain.

17. The method of claim 13, wherein the disease or condition is pain due to osteoarthritis.

18. The method of claim 13, wherein the disease or condition is post-operative pain.

19. The method of claim 13, wherein the disease or condition is osteoarthritis.

20. The method of claim 16, wherein the subject is a human.

21. A method of inhibiting the activity of a tropomyosin-related kinase, comprising contacting a tropomyosin-related kinase with an effective amount of a compound of claim 1 to inhibit the activity of said tropomyosin-related kinase.

22. The method of claim 21, wherein the tropomyosin-related kinase is tropomyosin-related kinase A.

23. The method of claim 21, wherein the tropomyosin-related kinase is tropomyosin-related kinase B.

24. The method of claim 21, wherein the tropomyosin-related kinase is tropomyosin-related kinase C.

25. A method of inhibiting the activity of a cellular receptor for colony stimulating factor-1, comprising contacting said cellular receptor for colony stimulating factor-1 with an effective amount of a compound of claim 1 to inhibit the activity of said cellular receptor for colony stimulating factor-1.

26. A method of preparing a compound of claim 1, comprising the steps of:
   a. admixing (i) a first solution containing acetone, water, and 3-(3-methoxy-4-((4-methoxybenzyl)oxy)benzyl)-6-(1-methyl-1H-pyrazol-4-yl)-3H-imidazo[4,5-b]pyridin-2-amine and (ii) an aliquot of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2 to provide a first mixture;
   b. maintaining the first mixture at a temperature in the range of from about 45° C. to about 55° C. for a duration of at least 2 hours, to produce a crystallization mixture containing an abundance of 3-(3-methoxy-4-((4-methoxybenzyl)oxy)benzyl)-6-(1-methyl-1H-pyrazol-4-yl)-3H-imidazo[4,5-b]pyridin-2-amine monohydrate in crystalline form exhibiting an X-ray powder diffraction pattern comprising peaks at the following diffraction angles (2θ): 14.9±0.2, 20.2±0.2, 20.7±0.2, 21.4±0.2, 25.1±0.2, 28.0±0.2, and 30.0±0.2; and
   c. isolating said compound of claim 1 from the crystallization mixture.

* * * * *